(12) United States Patent
Wallis et al.

(10) Patent No.: US 8,141,793 B2
(45) Date of Patent: Mar. 27, 2012

(54) GEL AIR FRESHENER AND METHOD OF UNSEALING SUCH GEL AIR FRESHENER

(75) Inventors: Judith A. Wallis, Chandler, AZ (US); Elizabeth Polaski, Scottsdale, AZ (US); Steven Carter, St. Louis, MO (US); Deborah J. Cowan, Scottsdale, AZ (US); Gary L. Berge, Crystal Lake, IL (US); Ronald Hedman, Crystal Lake, IL (US)

(73) Assignee: The Dial Corporation, Scottsdale, AZ (US)

( * ) Notice: Subject to any disclaimer, the term of this patent is extended or adjusted under 35 U.S.C. 154(b) by 511 days.

(21) Appl. No.: 12/502,747

(22) Filed: Jul. 14, 2009

(65) Prior Publication Data

US 2011/0011947 A1 Jan. 20, 2011

(51) Int. Cl.
*A24F 25/00* (2006.01)
(52) U.S. Cl. .................. 239/55; 239/44; 239/6
(58) Field of Classification Search .............. 239/34, 239/47, 51.5, 55, 57, 60, 43, 44, 6
See application file for complete search history.

(56) References Cited

U.S. PATENT DOCUMENTS

| | | |
|---|---|---|
| 1,612,449 A | 12/1926 | Lee |
| 3,165,220 A | 1/1965 | Haynes |
| 3,339,770 A | 9/1967 | Welgand |
| 4,501,376 A | 2/1985 | Bushby |
| 4,560,076 A | 12/1985 | Boik |
| 5,320,233 A | 6/1994 | Welch |
| 5,449,077 A | 9/1995 | Seidler |
| 5,529,201 A | 6/1996 | Tallent et al. |
| 6,015,054 A | 1/2000 | King et al. |
| 6,227,391 B1 | 5/2001 | King |
| 6,315,167 B2 | 11/2001 | Brecheisen et al. |
| 6,357,634 B1 | 3/2002 | Evans et al. |
| 7,182,213 B2 | 2/2007 | King |
| 7,198,170 B2 | 4/2007 | Herr |
| 7,246,713 B2 | 7/2007 | King |

(Continued)

FOREIGN PATENT DOCUMENTS

GB 2 319 513 A 5/1998

(Continued)

*Primary Examiner* — Davis Hwu
(74) *Attorney, Agent, or Firm* — Paul A. Pappalardo

(57) ABSTRACT

The present invention is a gel air freshener article of manufacture comprising a gel air freshener composition and a container that provides a method for unsealing and opening without undue exertion by the consumer. The article of manufacture according to the present invention includes the gel air freshener composition and a container comprising a base portion and axially displaceable cover in telescopic registry, wherein the cover is axially displaced away from the base portion by rotation. The unsealing of the container is achieved through the coordination of camming locks, which comprise an upper ramped surface, with spike-shaped locking wedges that comprise a beveled toe portion, elongated shaft portion and camming head portion. Rotation of the cover in a first direction relative to the base portion locks the toe end and shaft portions of the spike-shaped locking wedges beneath the camming locks. Rotation in a second opposite direction relative to the base portion backs the camming head portion of the spike-shaped wedges up the upper ramped surfaces of the camming locks such that the cover is axially distanced from the container, thus unsealing the cover from the base and breaking loose the gel air freshener composition bound inside surface of the cover. An optional pin-hole in the cover allows for pressure equalization of the momentary vacuum created when the cover is first unsealed and displaced.

16 Claims, 11 Drawing Sheets

U.S. PATENT DOCUMENTS

| | | |
|---|---|---|
| 7,331,491 B2 | 2/2008 | King |
| 7,461,755 B2 | 12/2008 | Manera et al. |
| 2007/0017937 A1 | 1/2007 | Berthelin et al. |
| 2007/0144999 A1 | 6/2007 | King |
| 2008/0017642 A1 | 1/2008 | King |

FOREIGN PATENT DOCUMENTS

| | | |
|---|---|---|
| GB | 2 409 200 A | 6/2005 |
| WO | WO 82/03058 A1 | 9/1982 |
| WO | WO 97/35773 A2 | 10/1997 |
| WO | WO 03/099672 A1 | 12/2003 |
| WO | WO 2008/095863 A1 | 8/2008 |

GEL AIR FRESHENER AND METHOD OF UNSEALING SUCH GEL AIR FRESHENER

FIELD OF INVENTION

The present invention relates to an air freshener containerized within a twist-to-unseal wide mouth container and in particular to an article of manufacture comprising a gel air freshener composition and container comprising a base portion and axially displaceable cover engageably enclosing the composition and method of unsealing the gel air freshener.

BACKGROUND

Gel air fresheners have existed for decades and are generally comprised of a mixture of natural and/or synthetic polymer, water, and fragrance that is solidified as a gel mass within a dispensing container. Such containerized products are formed from a hot liquid mixture that is poured into the dispensing container where the liquid mixture cools and gels. Such air fresheners are found in a variety of forms. For example, a gel air freshener may be provided in a simple open top cup-like container having a foil top that the user peels away and discards. Such a container is useful in providing a replacement cup of gel air freshener that fits within an institutional air freshener dispenser. Other systems may feature a foil and plastic laminated film wherein a non-permeable layer is peeled away and discarded leaving behind a permeable membrane layer still covering the product. In this way, a fragranced gel is exposed to the air to fragrance a room even though the air freshener mass cannot be physically touched. This system has been successfully employed in "gel-electric air fresheners" for many, many years. Larger weight gel air fresheners intended to operate at ambient conditions (i.e., passive gel air fresheners) may be solidified within a container comprising a base portion and a cover where both the base portion and the cover contain a substantial portion of the total solidified mass of air freshening gel. In such systems the cover is not completely removed and discarded because this would expose too large a surface of the gel product at once. In these systems the cover is instead pulled up from the base only to the extent that exposes the surface of product needed to fragrance a particular space. An exemplary product with such a displaceable cover is the Renuzit Adjustable® Air Freshener by Dial (Henkel). This conical shaped product features an axially displaceable cover that is "adjusted" in height to expose the fragranced gel mass to the extent desired. However, pulling up the cover of a brand new product is problematic because it is difficult to get the gel mass to release from the inside surface of the cover. The consumer has to assert force against a seal that was created when the hot liquid product, (initially poured through an access port in the top of the cover/base assembly), subsequently cooled within the assembled package. Although a jar of jelly may be thought of as having a vacuum seal that the consumer needs to overcome to remove the lid, the product (i.e., the jelly) is not contained in the closure, and therefore the product does not bind the closure to the container. Aside from the particular example of Renuzit Adjustable® containerized gel product, container systems having axially displaceable covers are found mostly in the food, beverage, and pharmaceutical markets, but only to the extent that the displaceable cover is simply a closure that does not contain any product itself.

Such closures usable to seal food, beverage, and pharmaceutical products in containers often feature closure assemblies based on coordinating lugs and cams rather than complementary screw threads. Lug and cam/hook/latch closure systems for containers offered many improvements over the traditional screw-thread closure arrangements. One improvement was that a lug and hook arrangement provided a child-resistant closure where the lugs of the closure cammed down and locked under complementary hooks or latches circumferentially spaced around the container neck. Another improvement was that a container closure could be designed to "snap on and thread off" from the container, thereby simplifying manufacturing. Also, the advent of tamper-evident closures required lug and cam arrangements that would cause a band to break away from the closure as the closure is unsealed from the container.

As indicated, the prior art has focused primarily on the need to seal closures to containers and to provide either tamper/child-resistance and/or tamper-evident features. But the prior art has been primarily concerned with containers and closure systems where product resides only in the container and not in the closure. That is, the prior art does not consider the situation where a solid gelled mass of material is solidified into both the container and a larger closure/cover where the cover also contributes to the available volume of the overall container. What is entirely absent in the literature is a way to adapt a lug/cam arrangement to assist in the unsealing and displacement of a cover from a container base where both the cover and the container base contain solidified material that has internally sealed the cover to the container base and has adhered to the inner surface of the cover.

SUMMARY OF THE INVENTION

In general, and by way of summary description and not by way of limitation, the present invention is an article of manufacturer comprising a gelled air freshener composition and a container that encases the solidified composition. The container further comprises a cover of generally conical shape reversibly coupled to a base portion, where both the cover and the base portion contribute substantially to the overall volume of the container, and where the container includes a system for the unsealing and axial displacement of the cover. In particular, a container is described that is adapted for a gel air freshener solidified in both the cover and base portion. In general the container of the present invention includes an unsealing system comprising complementary spike-shaped locking wedges and camming locks. The invention may also include an air vent (e.g. a pin-hole) usable to equalize pressure inside and outside the container as the cover is unsealed and displaced through the camming action. The present invention includes a method of unsealing a gel air freshener comprising the step of twisting the cover relative to the base portion wherein the head portions of the spike-shaped locking wedges ride up the ramped upper surface of the camming locks to unseal and vertically displace the cover from the base, dislodging the adhered gel mass from the inner surface of the cover.

DETAILED DESCRIPTION OF THE INVENTION

Figure 1:
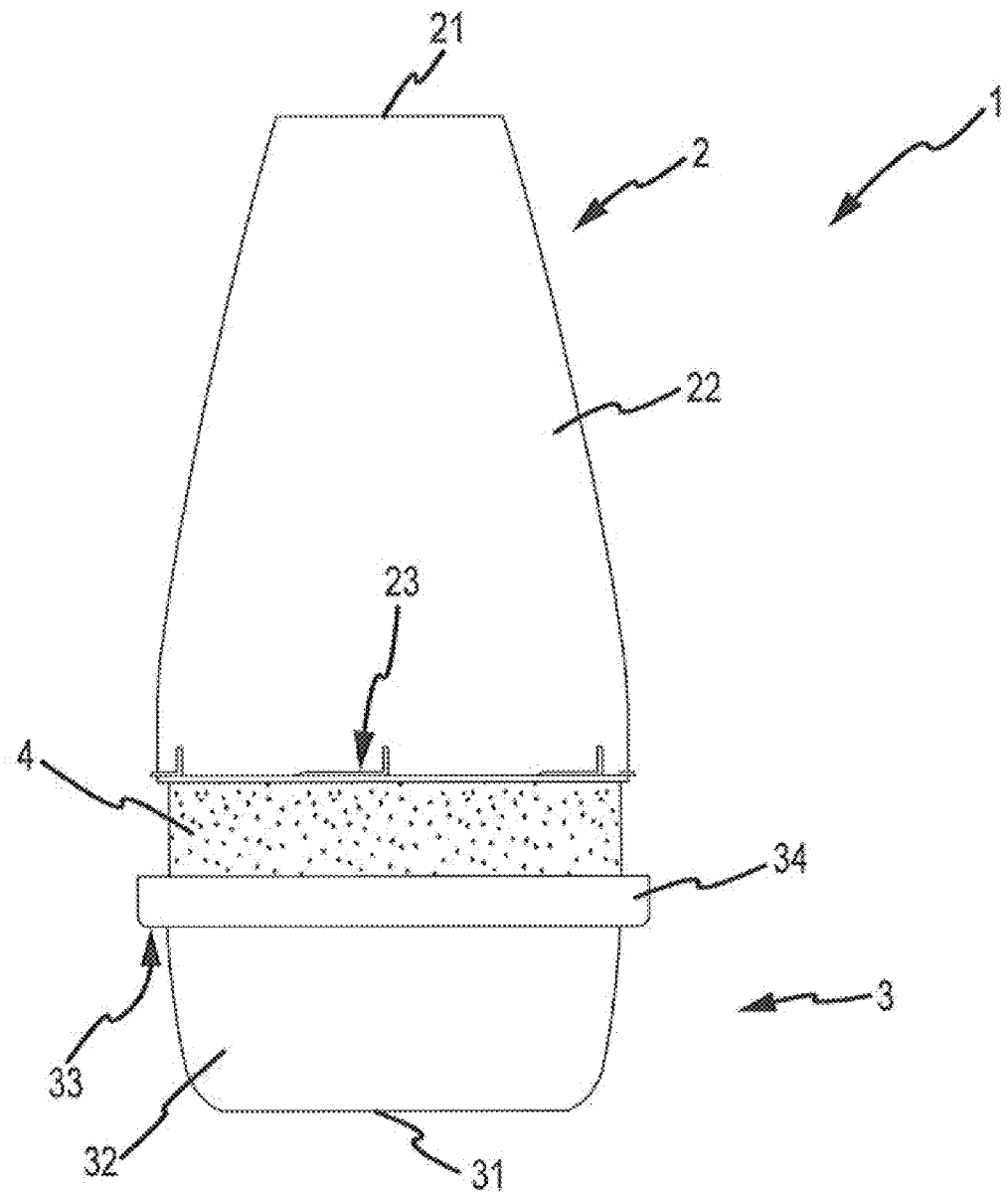
FIG. 1 is a front view of a gel air freshener article of the present invention in which the cover of the container is partly displaced vertically from the base portion of the container to expose the fragranced gel mass.

The following description is of exemplary embodiments only and is not intended to limit the scope, applicability or configuration of the invention in any way. Rather, the following description provides a convenient illustration for implementing exemplary embodiments of the invention. Various changes may be made in the function, size, and arrangement of the elements described without departing from the scope of the invention as set forth in the appended claims. Changes in shape and size of the overall air freshener do not depart from the intended scope of the invention. Additionally, the relative positions of certain complementary elements may be interchanged, and mirror images of certain unsymmetrical elements may be used, without departing from the spirit of the invention. Lastly, the container of the present invention is not limited by its materials of construction, although plastic is preferred. Most typical is to make these plastic parts from an injection or injection blow-molding process, and the plastic used may be any material known in the plastics industry for molded plastic parts (PP, PE, PVC, polycarbonate, polystyrene, polyethylene terephthalate, and the like).

For ease in describing the air freshener article and method of unsealing such while referencing the accompanying drawings, the product will be spatially oriented such that the bottom surface of the base portion sits relatively flat on a horizontal surface (such as a tabletop). Thus the cover will be referred to as moving vertically upwards away from the base portion when axially displaced to expose the gel air freshener composition inside. Likewise, the cover will be referred to as moving vertically downwards toward the base portion when closing off the gel composition. Thus the base portion is the "bottom portion" of the air freshener whereas the cover is the "top portion". Since the preferred cross-sectional configuration for the present invention is circular, and since certain structural elements are preferably circumferentially spaced around this shape, (i.e. the product preferably has rotational symmetry), designations such as "front", "back", "rear", "left", and "right" designations only make sense when the rotational orientation is fixed. Hence at times it will be necessary to describe an element that may happen to appear in the front, as opposed to the rear, of a particular view.

With that said, the present invention is a gel air freshener article that comprises a gelled air freshener composition and a "twist-to-unseal" wide mouth container that encases the composition, and a method of unsealing such product. The container of the present invention further comprises engageable base portion and cover, wherein the base portion and cover include complementary and coordinating camming locks and locking wedges to aid in the locking, unsealing, and axial displacement of the cover. Importantly, the base portion and the cover each contain a substantial portion of the solidified air freshener composition, and it is the coordination of the cams and locking wedges that enable the gel material to be easily broken free from the inside surface of the cover to start the axial displacement of the cover for the consumer.

Referring now to FIG. 1, the gel air freshener article of the present invention 1 comprises a gelled air freshening composition 4 containerized within a container defined by engageable cover 2 and base portion 3. As shown, the overall invention is preferably conically shaped, although an overall cylindrical shape would suffice as well. Conical shape is preferred because the cover is easier to pull up and off of the solidified conical-shaped air freshening gel mass therein once the seal is broken and axial movement started, whereas in a cylindrical product the cover would continuously bind with the gel mass during any axial displacement. Central to a "twist-to-unseal" design is of course a circular cross section. The exterior shape of the article substantially defines the internal space and therefore the gelled composition 4 would necessarily take on the conical shape of the container it was solidified in. It's important to recognize that the ratio in size of the base portion to the cover may be varied considerably, for example even to the extreme of from about 1:10 to about 10:1. What is depicted in FIG. 1 is about a 1:3 or 1:4 size ratio, and anywhere from about 1:4 to 4:1 is practical and desired. Notably and most importantly, the gel composition 4 is simultaneously molded in both the cover 2 and the base portion 3 as a single solid mass. This is possible by pouring the gel composition in its liquefied state through an access port in the top of the assembled container (i.e., with the cover 2 and base portion 3 fully engaged). In this way the liquid composition fills in all of the interior space defined by the assembled cover and base, where it then solidifies. As mentioned in the introduction, this manufacturing practice causes the sticking of the composition to the plastic parts and the need to have a way to easily unseal and start the displacement of the cover for the consumer.

Still referring to FIG. 1, the article 1 is shown partially opened such that the solidified gel composition 4 may be partially seen, and it is in this configuration that the product would provide air freshening (i.e. opened to liberate volatile fragrance from the gel). Cover 2 comprises a top wall 21 contiguously molded with conical or cylindrical sidewall 22. Cover 2 is preferably made from plastic, most preferably using an injection or injection blow-molding process. As will be described later, the cover may be molded with a closable access port at the top, for example by molding the plastic cover 2 minus a portion of, or minus the entire top wall 21. The cover also includes circumferentially spaced elongated spike-shaped locking wedges 23 that will be described below. In this particular rotational orientation shown, three of a total of six preferred locking wedges 23 are observable in whole or in part. Base portion 3 of the present invention comprises in combination; a bottom wall 31, a substantially cylindrical peripheral sidewall 32, an annular wall 33 extending radially outwardly near the top end of peripheral sidewall 32, and an annular axial skirt 34 extending upwardly from annular wall 33. As per the cover, the base portion 3 is preferably molded from plastic in an injection or injection blow-molding process.

Figure 2:
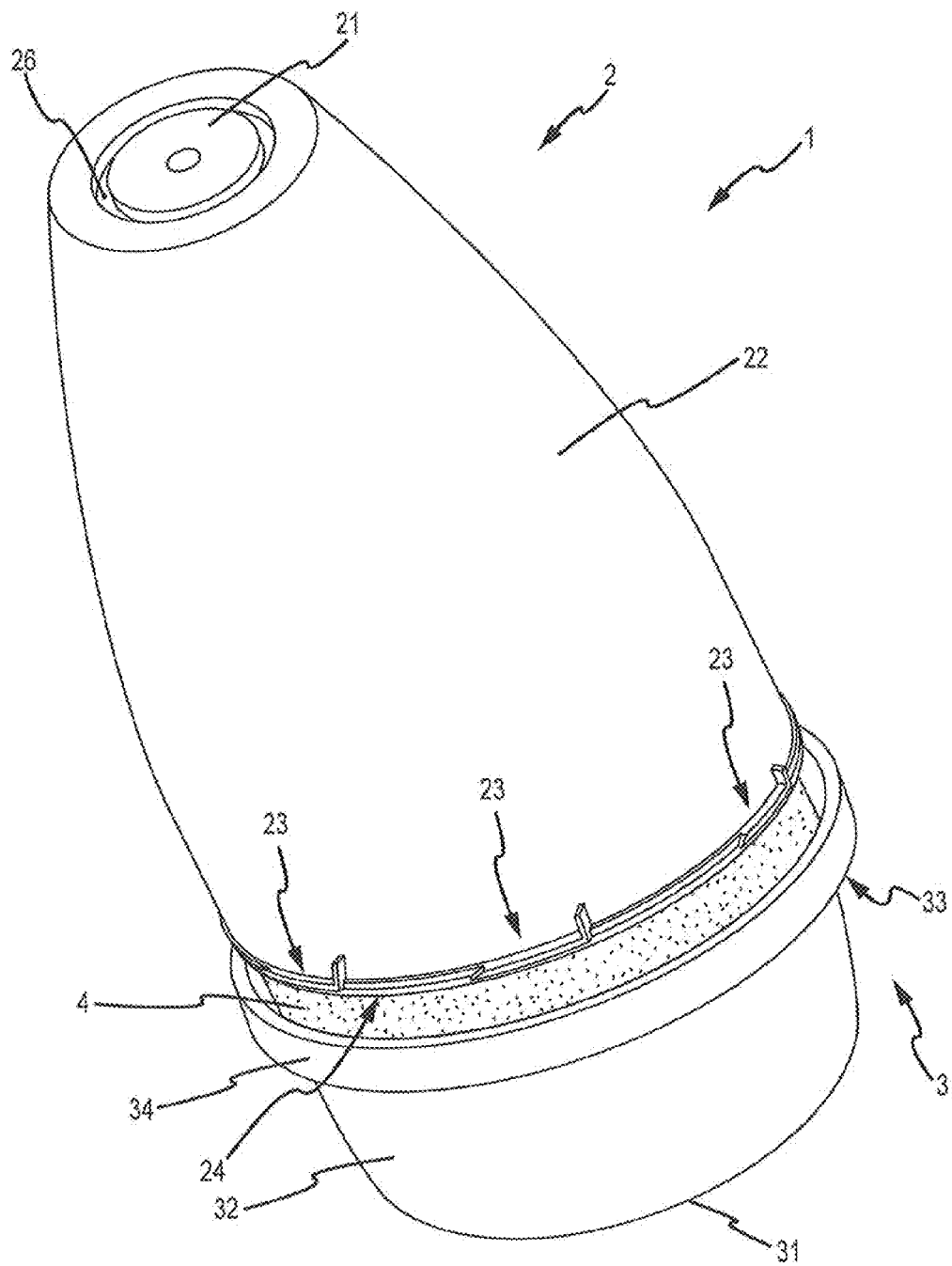
FIG. 2 is a perspective view of the gel air freshener of the present invention in which the cover of the container is partly displaced from the base portion of the container.

FIG. 2 represents a perspective view of the article 1 of the present invention. The top wall 21 of the cover 2 is now more visible, and is preferably relatively disc shaped. As will be described below, it is preferred that the top wall 21 be detachable from the sidewall 22 of the cover 2 to provide for a closeable filling port. Visible in this view are all of the elements previously described in FIG. 1, along with an optional air vent 26 positioned anywhere on the cover 2. Air vent 26 may be a small hole from about 1/32 of an inch to about 1/4 of an inch in diameter (i.e. a "pin-hole"). It serves as a pressure equalizing vent when the cover 2 is unsealed and displaced from the base portion 3 and also allows a way for the consumer to smell/sample the product fragrance in the store without opening it. It is most preferred to configure the vent hole 26 as a small pin-hole on a reversibly removable top wall 21 of the cover 2. Also shown in this figure is the bottom edge 24 of the cover 2 that is important in the sealing of the cover 2 onto the base portion 3.

Figure 3:
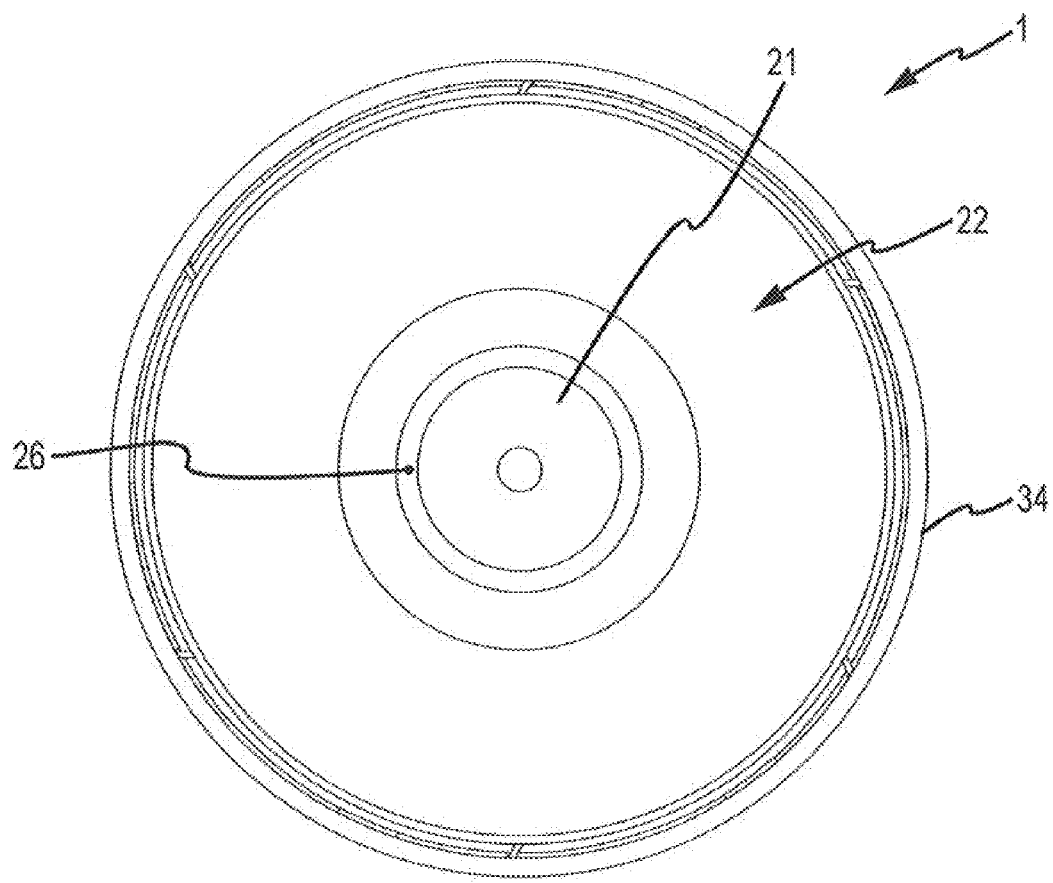
FIG. 3 is a top view of the gel air freshener of the present invention.

FIG. 3 is a top view of the article 1 of the present invention. Visible in this view is the top wall 21 and conical sidewall 22. As mentioned, these surfaces may be contiguously molded or alternatively the top surface 21 may be a reversibly removable "cap" that fits into the top of the cone shaped wall 22. Also visible in this view are the air vent 26 and the annular axial skirt 34.

Figure 4:
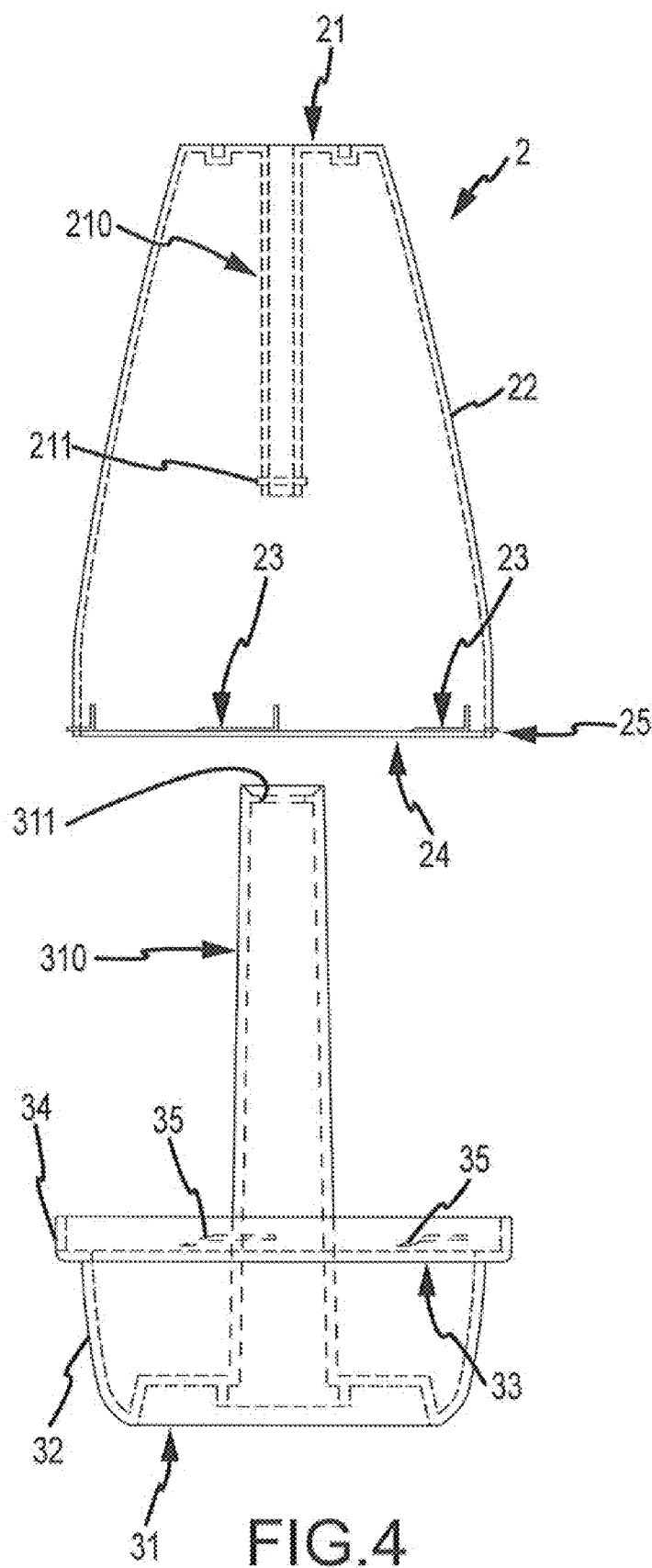
FIG. 4 is a front view of a gel air freshener container of the present invention comprising telescopically engageable cover and base portion, which are shown disengaged.

Referring now to FIG. 4, the air freshener of the present invention comprises a two-piece container defined by engageable base portion 3 and cover 2 as mentioned above. The fragranced gel mass is left out for clarity. The base portion 3 further comprises a bottom wall 31 contiguous with a substantially cylindrical peripheral wall 32. The bottom wall 31 and substantially cylindrical peripheral wall 32 define a first interior space that is open and cup-shaped and that is capable of containing a substantial portion of the gel air freshener composition. The base portion 3 preferably includes a first fastening element 310 configured as a hollow vertical protuberance emanating from the bottom wall 31 that is aligned for sliding/telescopic registry with a complementary fastening element provided inside the cover. First fastening element 310 preferably includes an internal circumferential flange 311 near its uppermost and open end that functions as a stop. The base portion also includes circumferentially spaced camming locks 35 (shown with dashed lines) preferably integrally molded onto the inside surface of the annular axial skirt 34. Preferably the base 3 includes at least two camming locks 35 and most preferably about six. It is most preferred that the camming locks 35 are circumferentially spaced around the inside of the skirt 34.

Still referring to FIG. 4, the cover 2 comprises a relatively flat and disc-shaped top wall 21 that is contiguous with conical sidewall 22. Sidewall 22 ends in a bottom edge 24 that is substantially circular due to the preferred conical shape of the cover 2. The cover preferably includes a circumferential flange 25 radially extending outwardly from a position just adjacent to the bottom edge 24. This flange 25, along with bottom edge 24, is useful in sealing the cover 2 to the base portion 3 (explained below). The top wall 21 and sidewall 22 of the cover 2 together define a second interior space that ends at the circular bottom edge 24. This second interior space is also capable of containing a substantial portion of the gel composition of the present invention, preferably even more than the base. Cover 2 also includes at least one elongated spike-shaped locking wedge 23. As will be described in more detail below, each wedge 23 is comprised of a beveled toe portion, elongated shank portion, and head portion. The toe and shank portions of each wedge 23 are dimensioned to fit and lock under the camming locks 35 when the cover is engaged onto the base portion and turned in a direction to register the wedges under the locks. Preferably there are matching pairs of wedges 23 and locks 35 and most preferably there are six pairs circumferentially placed around the inside of skirt 34 and outside of cover sidewall 22. However, the present invention is not limited as to the number of cams and wedges, or even that they be present in pairs. The minimum requirement is that the invention comprises at least one locking wedge 23 and at least two camming locks 35. In this way a single wedge can lock under the camming lock in front of it by turning the cover in a first direction, and may ramp up the second camming lock behind it by turning the cover in an opposite direction. The cover 2 also preferably includes a second fastening element 210 that is configured as a shaft or rod-like protuberance that extends downward from inside of top wall 21, hanging into the second interior space described. The second fastening element 210 is positioned axially and centrally to the conical or cylindrical sidewall 22 such that it may align and telescopically register with the first fastening element 310 protruding out from the base portion. Most simply, the telescopic assembly comprising the registered first and second fastening elements 210/310 may preferably be a telescoping rod and tube configuration. It is important to note that these elements may be reversed without change to the invention. That is, the tubular element 310 may be in the cover and the shaft or rod-like element 210 may be in the base portion. So long as the two elements of the fastening assembly align such that they may telescopically engage. An exterior retaining ring 211 may be provided on the rod-like second fastening element 210 to cooperate with the internal flange 311 positioned within the tubular first fastening element 310. In this way the rod-like element 210 may be aligned and pushed inside of the tubular element 310 and the flange/ring elements 211/311 may cooperate to prevent the cover 2 from being easily pulled completely back off the base portion 3. Thus fastening assembly 210/310 may allow for telescopic extension in length only to the point where the retaining ring 211 pulls up against the internal circumferential flange 311. Most importantly, fastening assembly 210/310 provides a controlled axial movement of the cover 2 vertically toward and away from the base portion 3 in the present invention. Pulling tip on the cover 2 (extending the telescopic assembly 210/310) exposes more of the gel composition contained as a solid mass therein, while pushing down on the cover 2 (collapsing the telescopic assembly 210/310) axially closes the cover back down on the base portion. As mentioned, it is preferred that the top wall 21 of cover 2 be removable to provide a filling port. Therefore it is most preferred that the top 21 and the fastening element 210 be molded as a single plastic part. Snapping this part into the conical shaped sidewall 22 completes the cover 2. Leaving this part off provides an access port for filling the assembled container with the liquefied gel composition. After filling, the single part comprising both 21 and 210 may be then snapped into place (while simultaneously guiding the elements 210/310 together) to complete the article 1 of the present invention.

Figure 5:
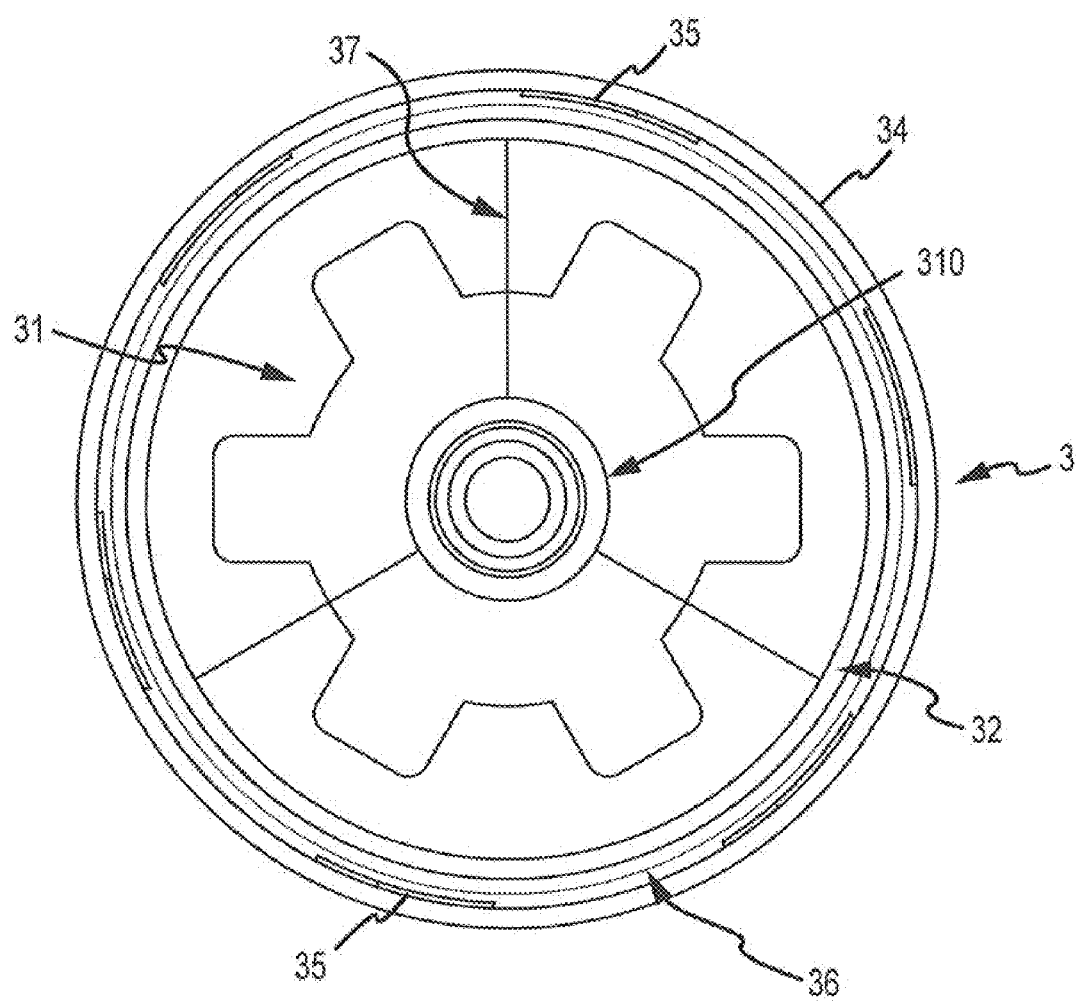
FIG. 5 is a top view of the base portion of the gel air freshener container of the present invention.

FIG. 5 is a top view of only the open base portion 3 of the container of the present invention. As mentioned, the base portion is preferably cup-shaped and includes a bottom wall 31, peripheral wall 32 and annular axial skirt 34. The floor of the radially extending annular wall 33 is seen in this top view and therein is preferably positioned a circular raised sealing bead 36 configured as a raised ridge concentric with, and positioned between, the peripheral wall 32 and the annular axial skirt 34. FIG. 5 shows the top view of six circumferentially spaced camming locks 35 positioned on the inside surface of the skirt 34. The tubular first fastening element 310 is visible along with anchoring means 37 partitioning the first interior space of the base portion. The anchoring means 37 holds the cast gel composition from rotation when the cover of the container is rotated relative to the base portion. One embodiment for the anchoring means may be a series of fins 37 radially connecting the first fastening element 310 with the inside of the peripheral wall 32 similar to the spokes of a wheel where 310 forms the "hub" and the peripheral wall 32 forms the "rim" of a wheel. Obviously any number of fins or spikes or other protuberances may be attached to either the fastening member 310 or the inside of the peripheral wall 32, or to both (such as these fins), so long as the anchoring means protrude into the interior space and reside within the gel in the base portion.

Figure 6:
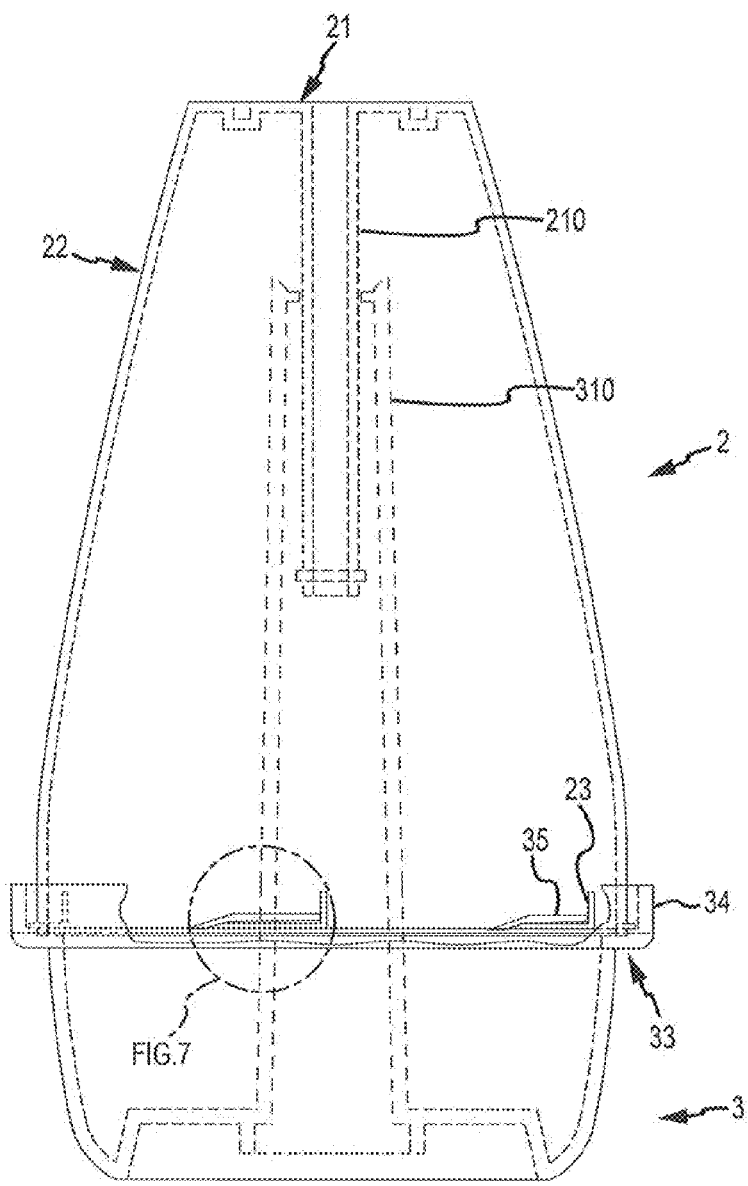
FIG. 6 is a front view of the assembled gel air freshener container of the present invention with part of the skirt of the base portion cut-away to reveal coordinating locking wedges and camming locks.

FIG. 6 illustrates the assembled container of the present article of manufacture without the gel composition cast therein. This view includes a cut-away of a surface portion of the skirt 34 in order to show the cooperation of the camming locks 35 and spike-shaped locking wedges 23. FIG. 6 shows the cover 2 fully engaged with base portion 3, wherein the bottom edge of the sidewall of the cover (element 24 in FIG. 4) is fully seated against the inside of the annular wall 33 (as will be described below). In this assembled configuration, fastening elements 210 and 310 are telescopically engaged and in the retracted position. With an exterior surface of the axial annular skirt 34 shown partially cut away, two pairs of coordinating cams and wedges are visible. As mentioned, elongated spike-shaped locking wedges 23, circumferentially spaced around the outside of cover 2 just adjacent to the circular bottom edge of the sidewall 22, are dimensioned and configured for registry under the camming locks 35 that are circumferentially spaced around the inside surface of the skirt 34. One of the pairs is shown circled and becomes the detail of FIG. 7 below. The locked configuration of the wedges and camming locks is the merchandisable configuration for the article of the present invention.

Figure 7:
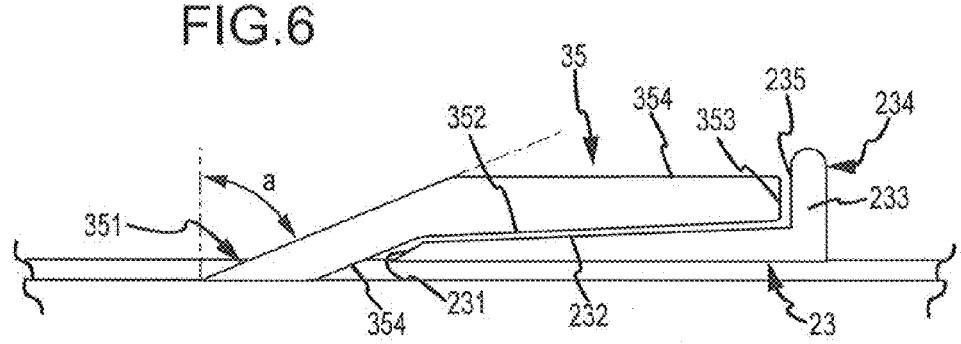
FIG. 7 is a detailed view of a spike-shaped locking wedge and camming lock in registry, wherein the beveled toe portion and elongated shank portion of the locking wedge are locked beneath the camming lock.

Referring now to FIG. 7, one of the elongated spike-shaped locking wedges 23 is shown in locking registry with one of the camming locks 35, the configuration that exists when the cover and base portion of the container are fully engaged, and when the cover is rotated in a direction relative to the base portion that locks the wedges under the camming locks. As emphasized, the relative location of the camming locks and the locking wedges may be reversed (i.e., locks on the cover versus locks on the base portion), and the cams and wedges may as exist as the "mirror images" of those depicted in the drawing figures, without exceeding the scope of the present invention. That is to say, the container may lock with clockwise or counter-clockwise rotation of the cover relative to the base. FIG. 7 shows the preferred configuration for the coordinating camming locks and locking wedges. As shown, camming lock 35 comprises an upwardly facing ramp surface 351 angled at from about 25 degrees to about 80 degrees from vertical, and most preferably at about 45-75 degrees. The upwardly facing ramp surface 351 provides the camming action, with the steepness of the angle "a" setting how high the cover will axially displace when the locking wedges ride up these inclines. The camming locks 35 further comprise a relatively horizontal portion 354 that terminates at a relatively flat and vertical back edge 353. The length of a camming lock in the present invention is somewhat arbitrary and may be from about ¼ of an inch to about 1 inch. Most preferably the camming locks are about ½-⅝ inch long and have a thickness of from about 1/16 to about ⅛ of an inch. As mentioned it is most preferred to incorporate about six camming locks around the container. Camming lock 35 also comprises an underside receiving notch defined by the downwardly facing angled surfaces 354 and 352. Downwardly facing surface 352 may be angled somewhat from true horizontal such that it also operates as a cam to help pull the cover down in tightly when the locking wedge 23 is jammed into registry within the receiving notch as shown in FIG. 7.

Referring still to FIG. 7, the elongated spike-shaped locking wedges 23 are preferably comprised of three contiguous portions like a spike or nail; namely an angled front toe or point 231; a slightly angled elongated shaft portion 232; and, a square or rectangular shaped head portion 233. The head portion 233 comprises both a forward stop surface 235 and a rear camming surface 234. As mentioned, a plurality of wedges 23 (e.g. six) are preferably molded circumferentially around the periphery of the sidewall of the cover, adjacent to the bottom open end, and most preferably directly on and contiguous with the circumferential flange (25 in FIG. 4) that is molded onto the sidewall of the cover just adjacent to the bottom edge. Each spike-shaped wedge 23 preferably measures from about ¼ of and inch to about 1 inch, and most preferably from about ½ to about ⅝ of an inch, dimensioned appropriately to coordinate with the camming locks 35.

As shown in FIG. 7, registry of a spike-shaped locking wedge 23 and a camming lock 35 involves the fitting of all of the toe 231 and shank 232 portions of the wedge 23 within the receiving notch of the camming lock 35, up to the point where the forward stop surface 235 of the head portion 233 butts up and stops against the vertical back edge 353 of the camming lock 35. Since the container is preferably filled from the top with liquefied (and often heated) air freshener composition, the cover and base portion of the container will preferably be in the locked and sealed configuration with the camming lock and locking wedge pairs 35/23 registered as per the pair illustrated in FIG. 7. The elongation of both elements 23 and 35 ensure a tight fit between them, much more so than provided in standard bottle closures that use ramps and lug provisions. Of course, both elements 23 and 35 are dimensioned and contoured relative to one another such that this registry is structurally possible.

Figure 8:
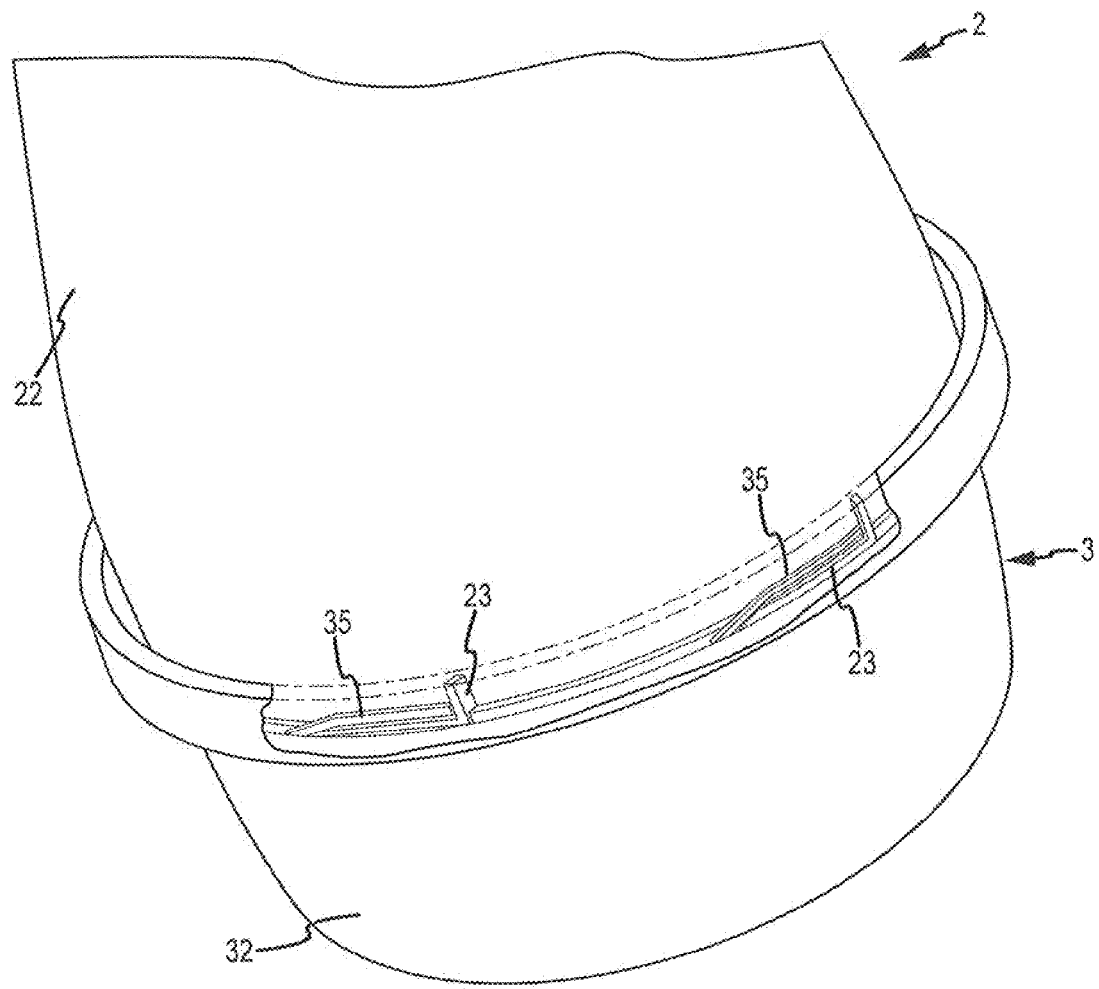
FIG. 8 is a cut-away view detailing the coordinating spike-shaped locking wedges and camming lock pairs when such pairs are in full registry.
Figure 9:
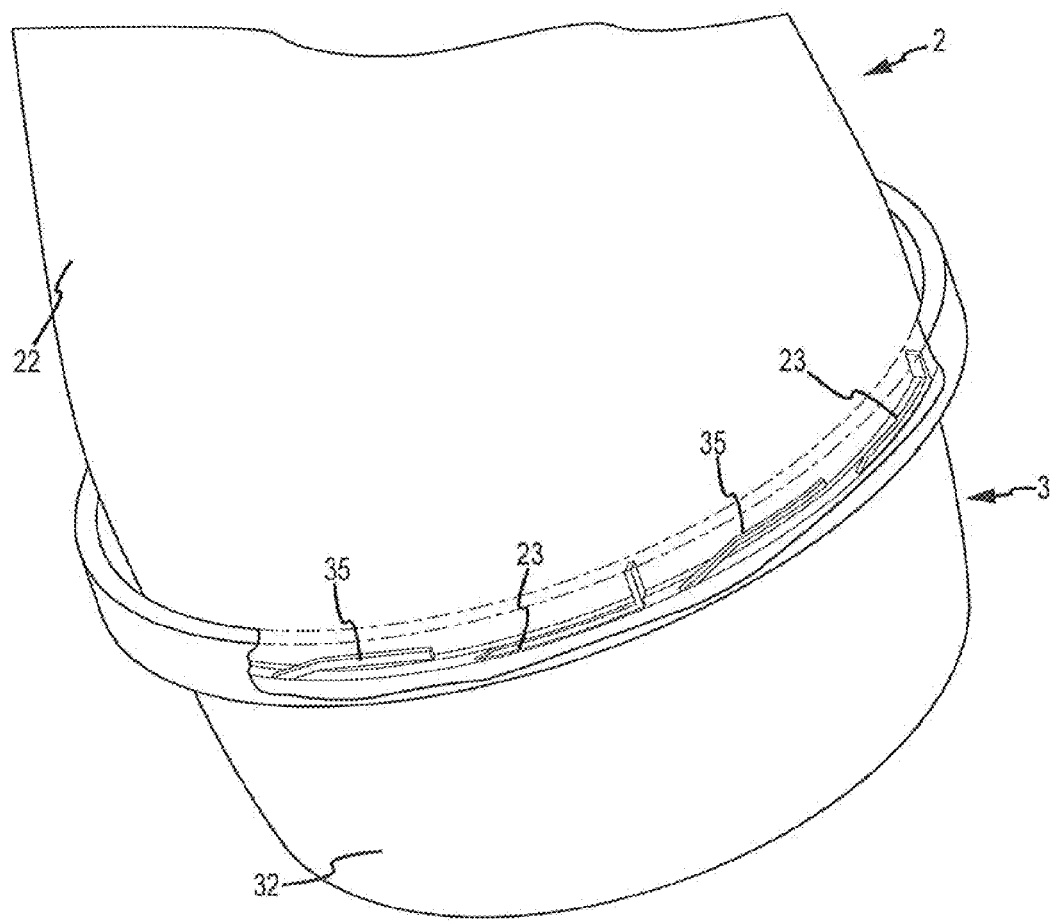
FIG. 9 is a cut-away view detailing the coordinating spike-shaped locking wedges and camming lock pairs when such pairs are rotated out of registry.
Figure 10:
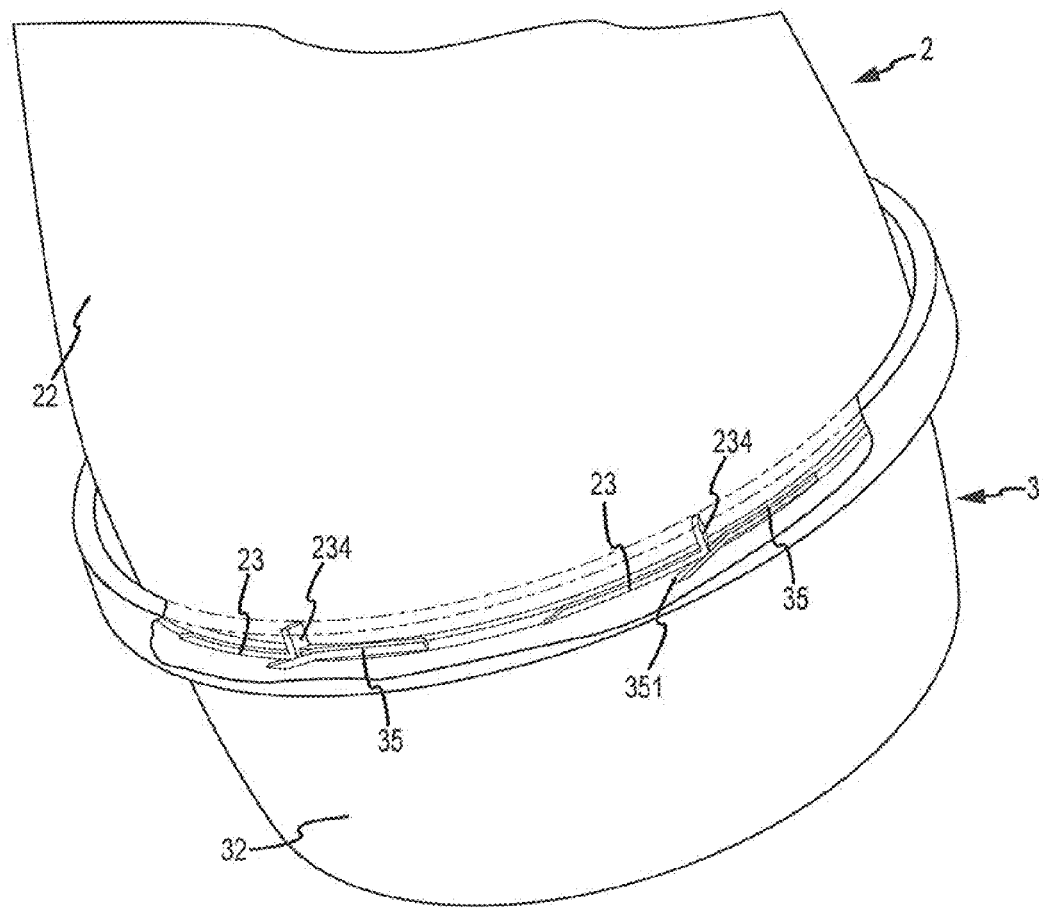
FIG. 10 is a cut-away view detailing the coordinating spike-shaped locking wedges and camming lock pairs where the head portion of each spike-shaped wedge has partially ramped up a complementary camming lock to axially displace the cover from the base portion.

FIGS. 8, 9, and 10 illustrate the changing positions of the locking wedges 23 and camming locks 35 when the cover 2 of the container is rotated relative to the base portion 3, (with the views featuring portions of the exterior surface of the skirt of the base portion cut-away, leaving the camming locks floating). As described thoroughly above and now referring to FIG. 8, the locked configuration for the container of the present article is shown with the spike-shaped locking wedges 23 in registry with the camming locks 35. Registry occurs by engaging the cover onto the base portion and then rotating the cover in a first direction relative to the base portion, where the pointed toe portion of the locking wedge points to the locking direction. For locking registry, the locking wedges are moved through rotation of the cover until the wedges jam within the receiving notches of the camming locks as described above. FIG. 9 shows the configuration where the cover is rotated in a second opposite direction such that the wedges 23 come out of registry with the camming locks 35. This same configuration is also achievable by simply engaging the cover down onto the base portion, guiding the spike-shaped wedges to positions between any two adjacent camming locks. Lastly, FIG. 10 illustrates an unsealed and partly opened configuration of the container that occurs when the cover is rotated in a direction that backs the rear facing camming surface 234 of the wedges 23 up the upwardly facing ramp surface 351 of the camming locks 35. In the configuration depicted in FIG. 10, the cover 2 has been axially displaced away from the base portion 3 and the article is thus unsealed. The changing configurations depicted sequentially with FIGS. 8, 9, and 10 relate to, and essentially illustrate, the method of unsealing an air freshener article of the present invention. That is, the consumer simply rotates the cover 2 relative to the base portion 3 in a direction that brings the wedges 23 out of registry with the camming locks 35 and subsequently cams the head of the wedges 23 up the ramping surfaces of the camming locks 35. This process breaks the cover free from the mass of gel solidified therein, and gives the consumer an easy start in lifting the cover up further to expose the air freshening gel to the ambient air and begin the air freshening process. Thus, the method of unsealing the gel air freshener article 1 of the present invention comprises the step of: rotating the cover 2 relative to the base portion 3 such that the head portion of the spike-shaped locking wedges cam-up the upper ramped surface of the camming locks to provide axial displacement of the cover away from the base portion, a movement which is vertically guided through the telescopic arrangement of the fastening elements in the cover and base, whereby the gel composition is broken loose from the inside of the cover as the cover is axially displaced. The air vent hole assists in the breaking of the seal by allowing air entry into the package to relieve the temporary vacuum formed as the cover is axially displaced by the camming action. Having thus broken the internal seal of the article, the consumer may now easily lift the cover further up to the height desired for air freshening.

Figure 11:
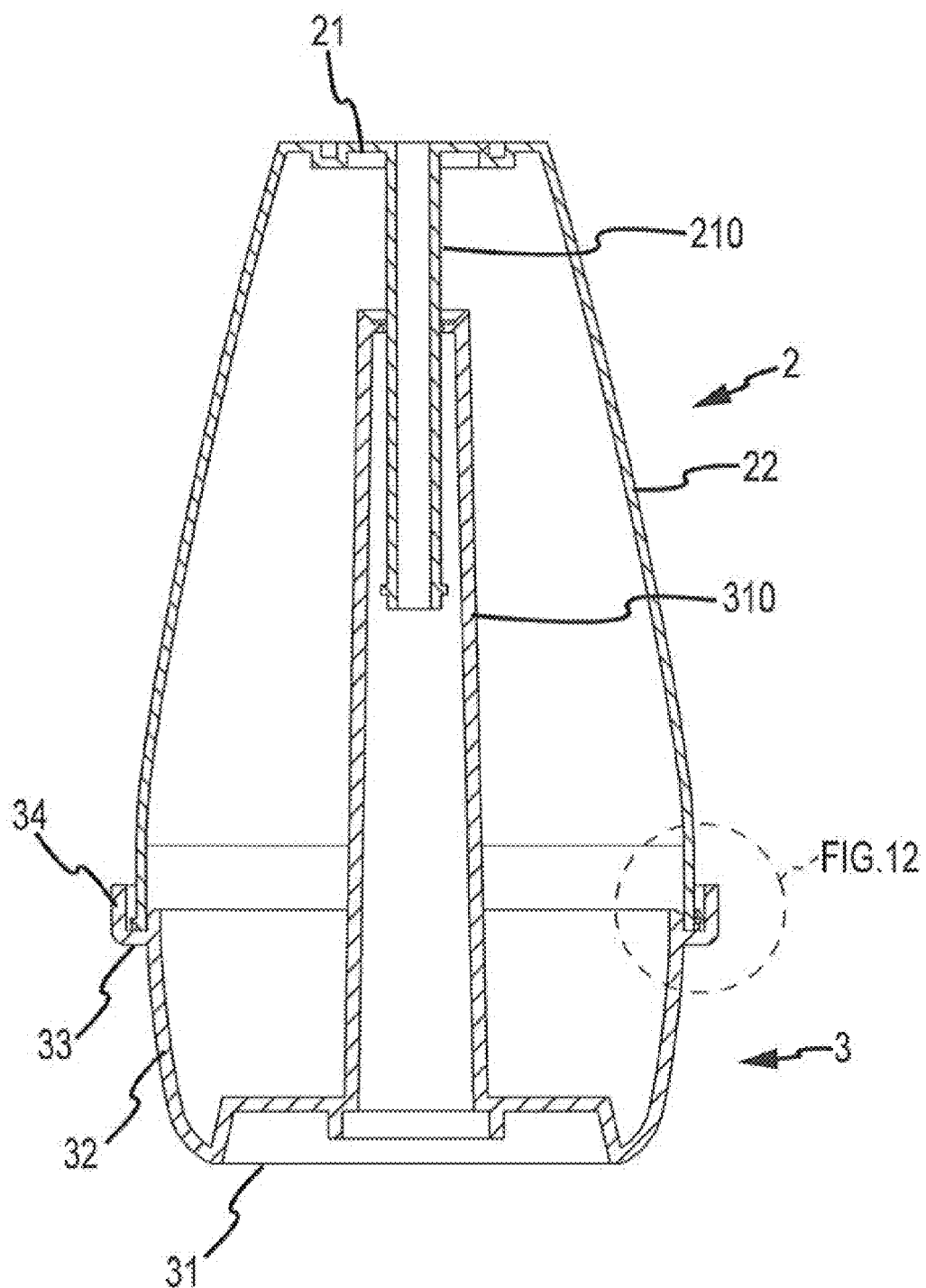
FIG. 11 is a cross-sectional view of the gel air freshener container of the present invention when assembled.
Figure 12:
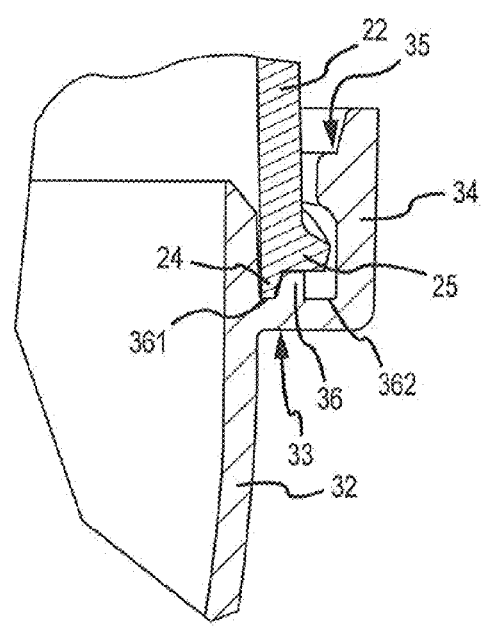
FIG. 12 is a cross-sectional detailed view of the fit between the bottom edge of the sidewall of the cover and a sealing track formed between a circumferential sealing bead and a concentric peripheral wall of the base portion.

FIGS. 11 and 12 are cross-sectional drawings that illustrate how the cover 2 and base portion 3 of the container of the present article 1 seal within the confines of the circumferential skirt. Referring now to FIG. 11, the cover 2 is shown engaged onto base portion 3 with concomitant telescopic engagement of fastening elements 210 and 310. Seen in this cross-sectional view is the sidewall 22 and top wail 21 of the cover 2, along with the bottom wall 31, peripheral wall 32, annular wall 33 and axial annular skirt 34 of the base portion 3. Most importantly, the circle drawn in FIG. 11 is enlarged into the detailed illustration of FIG. 12.

Referring now to FIG. 12 and as mentioned above, a circumferential sealing bead 36 is provided in the bottom of the circumferential sealing trough defined by the peripheral wall 32, annular wall 33 and annular axial skirt 34 as illustrated. This sealing bead 36 is preferential molded contiguously into the floor of the annular wall 33 as a raised ridge, for example about 1/32-1/16 of an inch in height, preferably positioned concentric with, and approximately radially between, the confines of the peripheral wall 32 and the annular axial skirt 34. As illustrated, the raised sealing bead 36 and the peripheral wall 32 define a narrow sealing track 361. This track may be configured to accommodate the bottom edge 24 of the sidewall 22 of the cover. Indeed, it is most preferred to chamfer the innermost top edge of the sealing bead at an angle of from about 2 to about 25 degrees and also to bevel the bottom edge 24 of the sidewall 22 of the cover such that the edge 24 can wedge into this narrowing crevasse 361. The circumferential flange 25 that is preferably provided on the sidewall 22 of the cover just above the bottom edge 24 forms a substantially horizontal flat surface that may sit and seal on top of the sealing bead 36 of the annular wall when the cover is pressed down onto the base portion. Thus, the method of sealing the container, either in preparation for filling with liquefied air freshener composition or when the consumer simply desires to stop the emanation of fragrance, is to push the cover axially down onto the base portion, allowing axial guidance by the retracting telescopic fastening elements described above, such that the beveled (knife-like) bottom edge 24 of the sidewall 22 of the cover frictionally jams into the narrowing sealing track 361.

The gel air freshener composition containerized within the container of the present invention preferably comprises an aqueous composition further comprising carrageenan, carboxymethy cellulose, hydroxyethyl cellulose, locus bean gum, guar gum, and/or other similar polysaccharide gallants, or alternatively synthetic polyacrylate or co-polymer gellants, fragrance, water, hydric solvents such as small molecular weight alkanols, diols, polyols, glycols and glycol ethers, and optional cross-linking ions such as $Ca^{2+}$. Such air freshening gels have been known for ages and are amply described in U.S. Pat. No. 2,927,055 (Lanzet); U.S. Pat. No. 3,969,280 (Sayce, et al.); and, U.S. Pat. No. 4,056,612 (Lin), each incorporated herein in their entireties, amongst many other prior art references. As mentioned, the ingredients are first combined at elevated temperature to produce a heated liquid solution which is then poured down through the top of the container where the base portion and cover are already assembled together and locked, but wherein the top of the cover has been left off. In this way a substantial portion of the gel air freshener is cast in both the base portion and the cover. Snapping the top of the cover back into place completes the article of the present invention.

The method of unsealing the present article 1 comprises the step of rotating the cover relative to the base portion, wherein the head portion of the spike-shaped locking wedges cam up the upper ramped surfaces of the camming locks to provide axial displacement of the cover away from the base portion. This action is vertically guided through extension of the telescopic arrangement of the fastening elements in the cover and base portion as described. Most importantly, this camming action breaks the cover free from the solidified gel composition molded in the cover. As mentioned a small vent hole may be provided in the cover to equilibrate the change in pressure that may occur when the seal is broken and the cover is first axially displaced through the camming action. This small degree of mechanically-assisted axial displacement of the cover is sufficient to get the consumer started in overcoming the seal inherent in the article. The consumer can now adjust the fragrance output from the article by moving the cover axially up or down as desired, such movement assisted by the telescopic assembly of the fastening elements.

We have thus described a unique gel air freshener article of manufacture that comprises both a gel air freshener composition and a container, where the container further comprises a cover and base portion that are unsealed from one another through the camming action of appropriately configured and coordinating camming locks and elongated spike-shaped locking wedges. This automatic camming action allows the consumer to overcome the seal created by casting the air freshener composition as a hot liquid into the assembled container and provides a method to easily break the cover free and off from the gel composition that is cast and adhering in the cover.

We claim:

1. An article of manufacture comprising:
 a. an air freshening gel composition; and
 b. a container having a base portion and cover engageable to form the container, said base portion and said cover each encasing a substantial portion of said composition;

wherein the base portion comprises a bottom wall and contiguous peripheral wall together defining a first interior space that terminates at a substantially circular top edge of the peripheral wall; a first fastening element protruding from said bottom wall within said first interior space; an annular wall extending radially outwardly from said peripheral wall adjacent to said top edge; an annular axial skirt contiguous with said annular wall and substantially parallel to said peripheral wall, said skirt having interior and exterior surfaces; and, at least two circumferentially spaced camming locks formed on and contiguous with said interior surface of said annular axial skirt; and wherein the cover comprises a top wall and contiguous sidewall together defining a second interior space that terminates at a substantially circular bottom edge of the sidewall; a second fastening element protruding from said top wall within said second interior space for telescopic registry with said first fastening element; at least one elongated spike-shaped locking wedge adjacent to and parallel to said bottom circular edge of said sidewall; and, wherein said spike-shaped locking wedge further comprises a beveled toe portion, an elongated shank portion, and a head portion; and wherein the at least one spike-shaped locking wedge and the camming locks are dimensioned and configured for registry to lock said cover to said base portion and for mutual cooperation to axially displace said cover away from said base portion.

2. The article of claim 1, wherein said top of said cover and said second fastening element protruding therefrom comprise a single integrally molded part that is detachable from said sidewall to provide an opening in said cover, wherein said container assembled through engagement of said cover and said base portion is fillable with said composition through said opening provided when said integrally molded part is detached from said sidewall of said cover.

3. The article of claim 1, wherein said cover further includes a circumferential flange positioned adjacent to said bottom edge of said sidewall and projecting radially outwardly therefrom.

4. The article of claim 1, further including more than two camming locks circumferentially spaced around the inside surface of said annular axial skirt.

5. The article of claim 4, further including more than one spike-shaped locking wedge circumferentially spaced around and parallel to the said bottom edge of said sidewall of said cover.

6. The article of claim 5, wherein said spike-shaped locking wedges and camming locks comprise six pair for registry and cooperation.

7. The article of claim 1, wherein said bottom circular edge of said sidewall of said cover is finished in a knife-edge bevel having an angle of from about 10 degrees to about 25 degrees from vertical.

8. The article of claim 7, wherein said radially extending axial wall further includes a circular sealing bead concentric with and juxtaposed between said peripheral wall of said base portion and said annular axial skirt, and wherein said sealing bead is chamfered at between about 10 degrees and 25 degrees on the edge closest said peripheral wall in order to provide a narrowing sealing track between said sealing bead and said peripheral wall to accommodate said beveled bottom circular edge of said sidewall of said cover.

9. The article of claim 1, further including an anchoring means positioned within said first interior space to secure a portion of said gel composition from movement within said base portion.

10. The article of claim 9, wherein said anchoring means comprises one or more fins or spikes attached to any of said bottom wall, peripheral wall, and first fastening element.

11. The article of claim 1, further including a vent hole configured through said cover.

12. The article of claim 1, wherein said composition comprises a liquid carrier, a polymeric gellant and fragrance oil.

13. The article of claim 12, wherein said polymeric gellant is chosen from the group consisting of carrageenan, carboxymethyl cellulose, hydroxyethyl cellulose, locust bean gum, guar gum, polyacrylate, and acrylic co-polymers, and mixtures thereof.

14. The article of claim 12, wherein said liquid carrier is chosen from the group consisting of water, alkanols, diols, polyols, and glycol ethers, and mixtures thereof.

15. A method of unsealing an article of manufacture, wherein the article of manufacture includes:
 a. an air freshening gel composition; and
 b. a container having a base portion and cover engageable to form the container, said base portion and said cover each encasing a substantial portion of said composition;
  wherein the base portion comprises a bottom wall and contiguous peripheral wall together defining a first interior space that terminates at a substantially circular top edge of the peripheral wall; a first fastening element protruding from said bottom wall within said first interior space; an annular wall extending radially outwardly from said peripheral wall adjacent to said top edge; an annular axial skirt contiguous with said annular wall and substantially parallel to said peripheral wall, said skirt having interior and exterior surfaces; and, at least two circumferentially spaced camming locks formed on and contiguous with said interior surface of said annular axial skirt; and
  wherein the cover comprises a top wall and contiguous sidewall together defining a second interior space that terminates at a substantially circular bottom edge of the sidewall; a second fastening element protruding from said top wall within said second interior space for telescopic registry with said first fastening element; at least one elongated spike-shaped locking wedge adjacent to and parallel to said bottom circular edge of said sidewall; and, wherein said spike-shaped locking wedge further comprises a beveled toe portion, an elongated shank portion, and a head portion; and wherein the at least one spike-shaped locking wedge and the camming locks are dimensioned and configured for registry to lock said cover to said base portion and for mutual cooperation to axially displace said cover away from said base portion;
 wherein said method comprises the step of:
  rotating said cover relative to said base portion wherein said head portion of said spike-shaped locking wedge cams up said camming lock to provide axial displacement of said cover away from said base portion, vertically guided through said telescopic arrangement of said first and second fastening elements, and wherein said gel composition is broken loose from the inside of said cover as said cover is axially displaced.

16. A method of producing an article of manufacture, wherein the article of manufacture includes:
 a. A liquid air freshening composition capable of gelling into a solid mass; and b. a container having a base portion and cover engageable to form the container, said base portion and said cover each encasing a substantial portion of said composition; wherein the base portion comprises a bottom wall and contiguous peripheral wall together defining a first interior space that terminates at a substantially circular top edge of the peripheral wall; a first fastening element protruding from said bottom wall within said first interior space; an annular wall extending radially outwardly from said peripheral wall adjacent to said top edge; an annular axial skirt contiguous with said annular wall and substantially parallel to said peripheral wall, said skirt having interior and exterior surfaces; and, at least two circumferentially spaced camming locks formed on and contiguous with said interior surface of said annular axial skirt; and wherein the cover comprises a top wall and contiguous sidewall together defining a second interior space that terminates at a substantially circular bottom edge of the sidewall; a second fastening element protruding from said top wall within said second interior space for telescopic registry with said first fastening element, at least one elongated spike-shaped locking wedge adjacent to and parallel to said bottom circular edge of said sidewall; and, wherein said spike-shaped locking wedge further comprises a beveled toe portion, an elongated shank portion, and a head portion;

wherein the at least one spike-shaped locking wedge and the camming locks are dimensioned and configured for registry to lock said cover to said base portion and for mutual cooperation to axially displace said cover away from said base portion; and wherein said top of said cover and said second fastening element protruding therefrom comprise a single integrally molded part that is reversibly detachable from said sidewall to provide an opening in said cover, wherein said container assembled through engagement of said cover and said base portion is fillable with said liquid composition through said opening provided when said integrally molded part is detached from said sidewall of said cover;

wherein said method comprises the steps of:

providing said container with said cover engaged on said base portion, said spike-shaped locking wedges in registry with said camming locks, and said integrally molded part comprising said top and said second fastening element detached from said sidewall of said cover to provide an opening in said cover;

providing said composition in a liquefied state;

pouring said liquid composition through said opening to fill both first interior space of said base portion and said second interior space of said cover;

attaching said integrally molded part comprising said top and said second fastening element onto said sidewall of said cover while simultaneously connecting said first and second fastening elements in telescopic registry; and allowing said liquid composition to gel into a solid mass within said container.

\* \* \* \* \*